United States Patent [19]
Binienda et al.

[11] Patent Number: 5,777,211
[45] Date of Patent: Jul. 7, 1998

[54] METHOD TO DETERMINE THE REMAINING USEFUL LIFE OF AUTOMATIC TRANSMISSION FLUID

[75] Inventors: Gary J. Binienda, Troy; Nabil M. Issa, Detroit; Hans Dourra, Dearborn; Spyros E. Drutis, Clarkston; Samer H. Halawi, Madison Heights, all of Mich.

[73] Assignee: Chrysler Corporation, Auburn Hills, Mich.

[21] Appl. No.: 758,140

[22] Filed: Nov. 25, 1996

[51] Int. Cl.$^6$ .................................................. G01N 33/26
[52] U.S. Cl. ................................... 73/53.05; 73/118.1
[58] Field of Search ............................. 73/54.02, 53.01, 73/53.05, 117.2, 118.1; 364/431.061, 424.097, 424.098; 475/158

[56] References Cited

U.S. PATENT DOCUMENTS

| | | |
|---|---|---|
| 3,693,448 | 9/1972 | Seltzer .................................. 374/142 |
| 4,258,421 | 3/1981 | Juhasz et al. . |
| 4,506,337 | 3/1985 | Yasuhara . |
| 4,525,782 | 6/1985 | Wohlfarth et al. . |
| 4,533,900 | 8/1985 | Muhlberger et al. . |
| 4,677,847 | 7/1987 | Sawatari et al. . |
| 4,694,793 | 9/1987 | Kawakita et al. . |
| 4,706,193 | 11/1987 | Imajo et al. . |
| 4,742,476 | 5/1988 | Schwartz et al. . |
| 4,796,204 | 1/1989 | Inoue . |
| 4,847,768 | 7/1989 | Schwartz et al. . |
| 4,862,393 | 8/1989 | Reid et al. . |
| 4,970,492 | 11/1990 | King . |
| 5,060,156 | 10/1991 | Vajgart et al. . |
| 5,107,724 | 4/1992 | Takizawa ................................ 477/97 |
| 5,173,856 | 12/1992 | Purnell et al. . |
| 5,267,158 | 11/1993 | Sakaguchi et al. ............. 364/424.097 |
| 5,318,449 | 6/1994 | Schoell et al. . |
| 5,325,082 | 6/1994 | Rodriguez . |
| 5,337,630 | 8/1994 | Sakai et al. .................... 364/424.086 |
| 5,377,531 | 1/1995 | Gomm .................................. 73/53.05 |
| 5,382,942 | 1/1995 | Raffa et al. . |

*Primary Examiner*—Michael Brock
*Assistant Examiner*—Jay L. Politzer
*Attorney, Agent, or Firm*—Roland A. Fuller, III

[57] ABSTRACT

A method of determining the remaining useful life of automatic transmission fluid used in an automatic transmission or transaxle is provided. A multiplicity of vehicles having the same type of automatic transmission or transaxle are monitored and data on factors bearing on the useful life of automatic transmission fluid are collected. Weighted constants are derived for each factor. The automatic transmission controller is then programmed to monitor the operation of the automatic transmission or transaxle and collect data on the factors that bear on the useful life of the automatic transmission fluid. Based on the collected data and weighted constants, the remaining useful life of the automatic transmission fluid is determined.

5 Claims, 11 Drawing Sheets

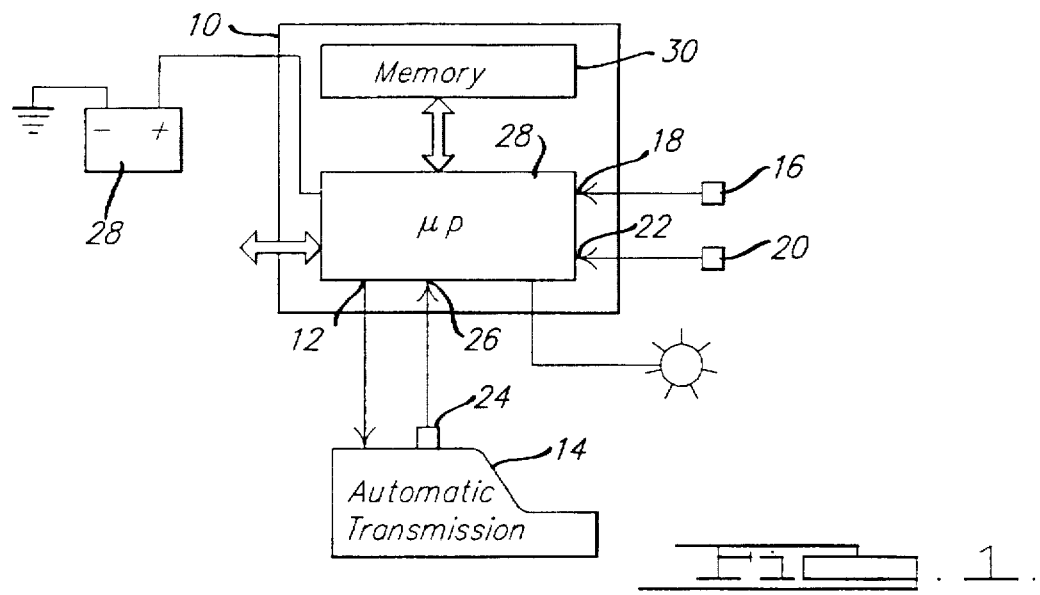
FIG. 1.
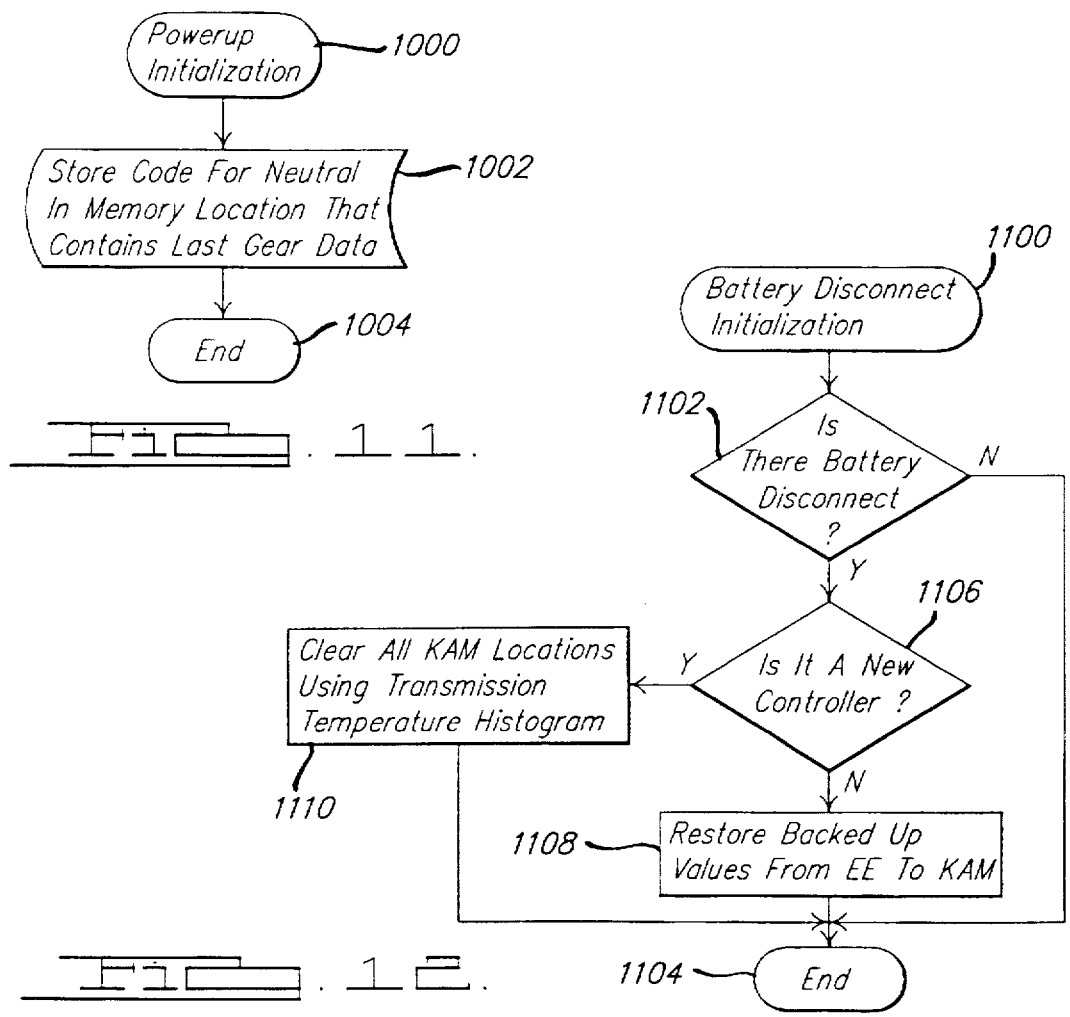
FIG. 11.
FIG. 12.

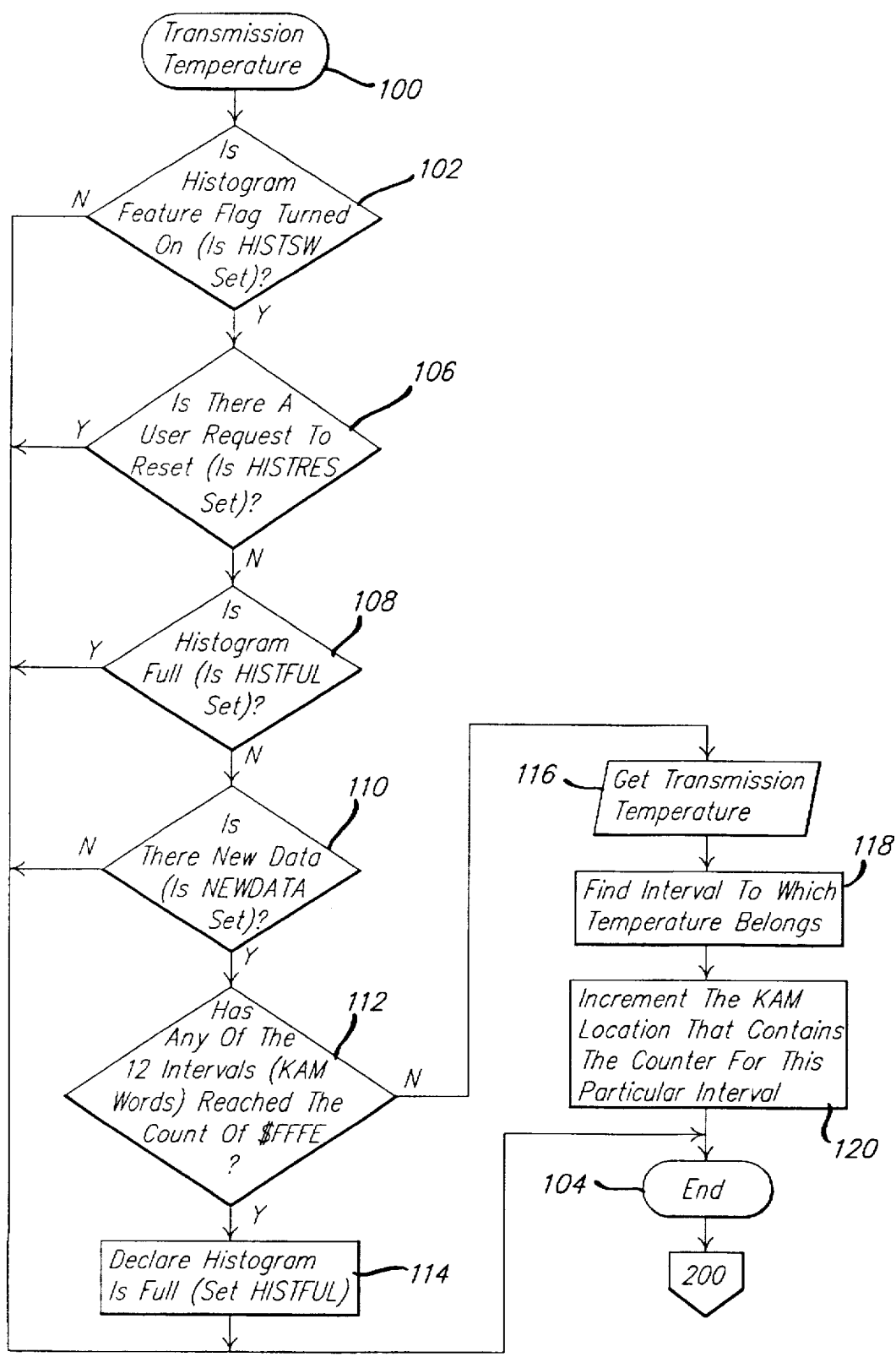

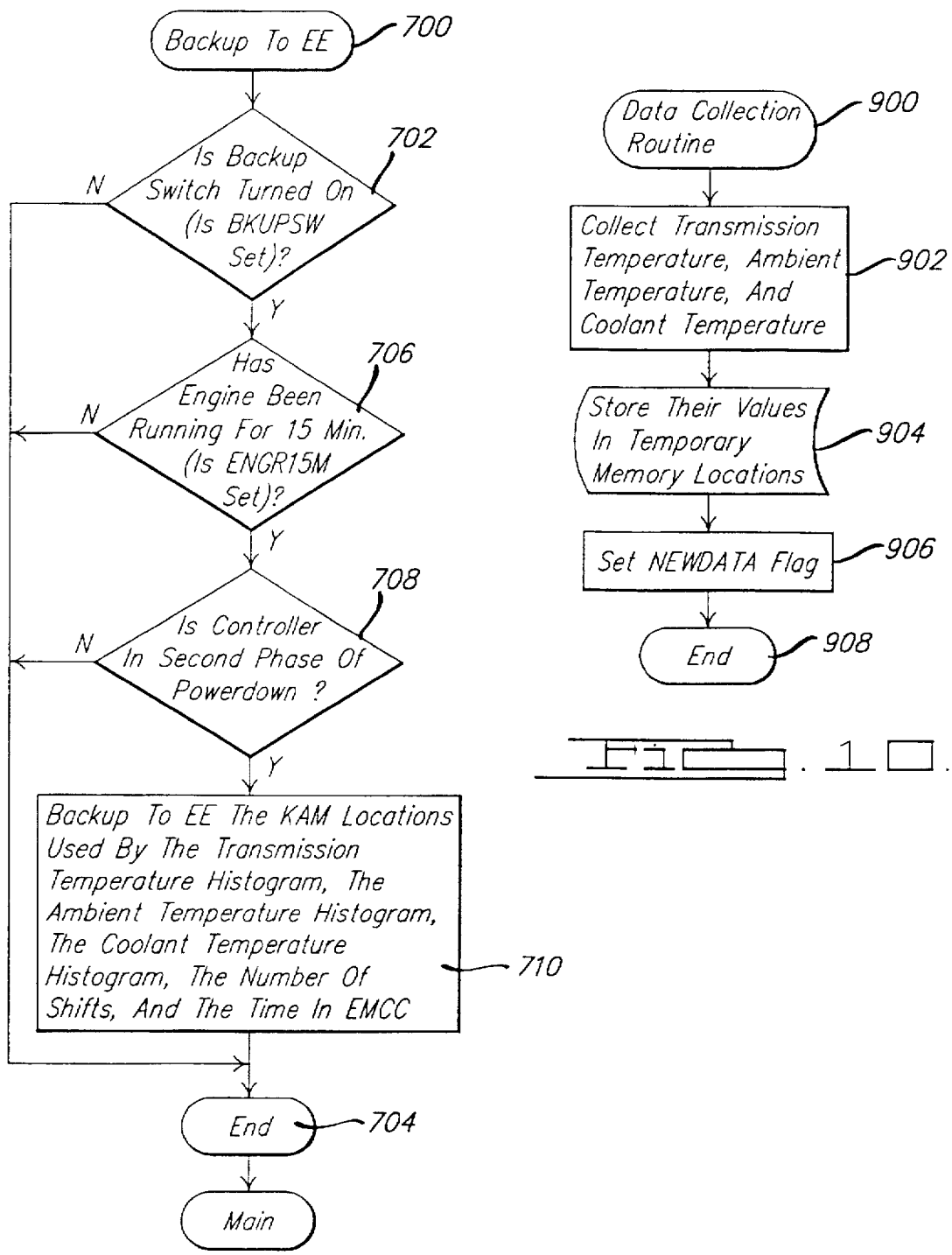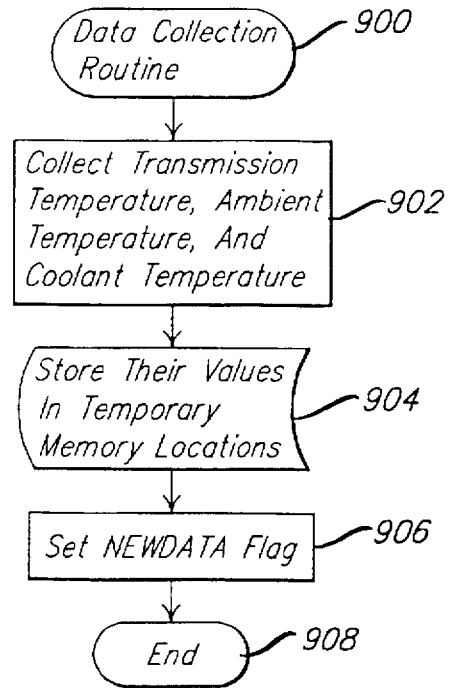

METHOD TO DETERMINE THE REMAINING USEFUL LIFE OF AUTOMATIC TRANSMISSION FLUID

This invention pertains to a method and apparatus for determining the remaining useful life of fluid used in automatic transmissions and automatic transaxles.

BACKGROUND

Automatic transmission fluid used in automatic transmissions and automatic transaxles has a finite useful life. When this useful life is exceeded, the fluid has degraded to the point where its continued use may adversely affect the operation of the automatic transmission or transaxle. To prevent this from happening, the automatic transmission fluid must be changed before it reaches the end of its useful life. This is typically done at periodic intervals, usually based on mileage. For example, the owner manuals of automobiles recommend changing the automatic transmission fluid after a certain number of miles, such as every thirty thousand miles.

While changing the automatic transmission fluid at periodic mileage intervals is an effective and convenient way to avoid exceeding the useful life of the fluid, it has some disadvantages. Mileage is a rough way of approximating the useful life of automatic transmission fluid in that represents an approximation of a number of factors which actually determine the useful life of automatic transmission fluid, such as transmission temperature, ambient temperature, coolant temperature, number of shifts, and the like. As such, the useful life of automatic transmission fluid can vary from individual car to individual car depending on how the car has been driven and the climate and geographic conditions in which it has been driven. For example, the automatic transmission fluid in a car driven mainly on the freeway at a steady speed in a temperate climate will have a longer useful life than the automatic transmission fluid in a car driven under stop and go conditions in a hot climate, such as a taxi-cab driven during the summer in a city such as Phoenix. In the former case, the automatic transmission fluid may well have a significant amount of its useful life left at the end of the periodic mileage interval whereas in the latter case, its useful life may have been exceeded.

It would be desirable to be able to determine the remaining useful life of automatic transmission fluid based on the specific factors that affect it and alert the driver of a vehicle that the automatic transmission fluid needs to be changed when it reaches the end of its useful life. However, to do so, requires taking into account the characteristics of the type or model of automatic transmission or transaxle in that automatic transmission fluid used in one type of automatic transmission or transaxle may have a different useful life than if used in a second type of transmission or transaxle even though operating under identical conditions.

It is an object of this invention to provide a more precise method of determining the remaining useful life of automatic transmission fluid and alerting the driver of a vehicle that the automatic transmission fluid needs to be changed when it reaches the end of its useful life that takes into account the characteristics of the transmission type as well as specific factors relating to the conditions under which the automatic transmission or transaxle has been operating.

SUMMARY OF THE INVENTION

In accordance with this invention, a method of determining the remaining useful life of automatic transmission fluid used in an automatic transmission or transaxle is provided. A multiplicity of vehicles having the same type of automatic transmission or transaxle are monitored and data on factors bearing on the useful life of automatic transmission fluid are collected. Weighted constants are derived for each factor. The automatic transmission controller is then programmed to monitor the operation of the automatic transmission or transaxle and collect data on the factors that bear on the useful life of the automatic transmission fluid. Based on the collected data and weighted constants, the remaining useful life of the automatic transmission fluid is determined.

BRIEF DESCRIPTION OF THE DRAWINGS

Additional features and advantages of the invention will become apparent to those skilled in the art upon consideration of the following detailed description of a preferred embodiment exemplifying the best mode of carrying out the invention as presently perceived. The detailed description particularly refers to the accompanying figures in which:

FIG. 1 is a block diagram of an automatic transmission/ transmission controller;

FIGS. 2–12 are flow charts of programs executed by an automatic transmission controller in accordance with this invention;

FIG. 13 is a histogram of transmission operating temperature;

DETAILED DESCRIPTION

Figure 3:
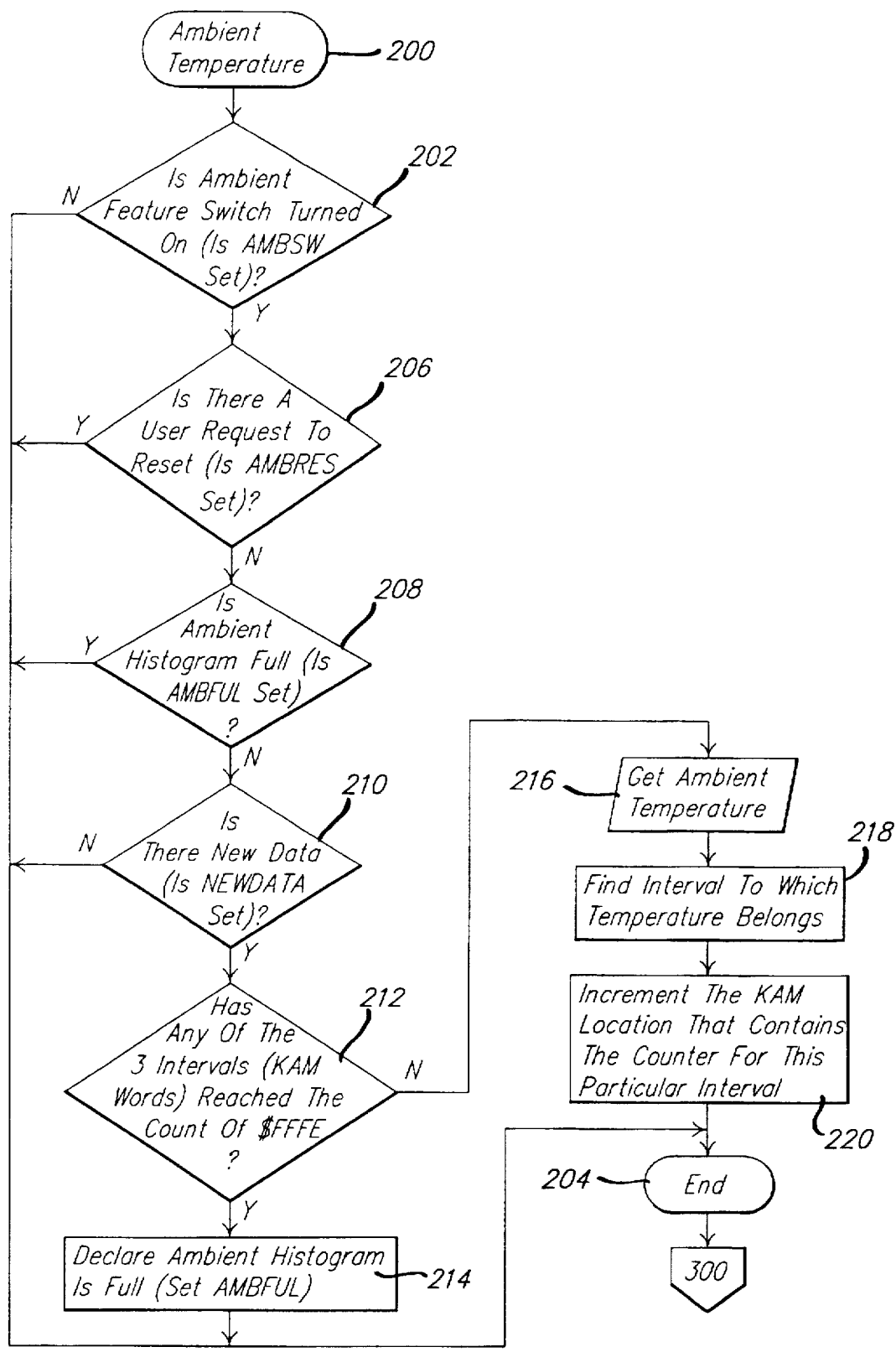

This invention is to determine the remaining useful life of automatic transmission fluid from a number of factors which determine its useful life and alert the driver of a vehicle that the automatic transmission fluid needs to be changed when it reaches the end of its useful life. To do this, the useful life of automatic transmission fluid must first be determined as a function of the factors which bear on it. Once the useful life of automatic transmission fluid is determined as a function of these factors, these factors can then be monitored in individual vehicles and, based on the monitoring of these factors, the remaining useful life of the automatic transmission fluid determined. The driver of the vehicle can then be alerted, such as by the illumination of a light in the vehicle's instrument panel, that the automatic transmission fluid has reached the end of its useful life and needs to be changed.

A number of factors affect the useful life of automatic transmission fluid. These factors include: operating temperature history (accumulated time at which the automatic transmission fluid has been at various temperatures during operation), ambient temperature history, coolant temperature history, number of shifts, time in electronic modulation of the converter clutch (EMCC), torque history during EMCC (history of torque levels during EMCC), accumulated mileage, accumulated shear during EMCC and accumulated shear during shifts. Shear during an EMCC is a function of time during that EMCC $[T_e]$, slip during that EMCC $[S_e]$, clutch disk area $[A]$ of the transmission or transaxle and a weighted factor $[K]$. Shear during a shift is a function of time during that shift $[T_s]$, slip during that shift $[S_s]$, clutch disk area $[A]$ of the transmission or transaxle and a weighted factor $[K_s]$. Slip is defined during partial lockup as engine speed minus the turbine speed of the transmission or transaxle. $K_e$ and $K_s$ are determined from data collected related to the above factors, as discussed below. Slip during shift is defined as $R_i$ times turbine speed minus outspeed, where $R_i$ is the gear ratio.

While each of these factors bears on the useful life of automatic transmission fluid, they do not have equal weight. Also, their weight may vary depending on the model of transmission or transaxle, or between different vehicle models using the same model transmission or transaxle. Therefore, to determine the useful life of automatic transmission fluid for a particular model of transmission or transaxle, historical data of the factors bearing on the useful life of the automatic transmission fluid must be accumulated for a statistically relevant sample size of vehicles in which the particular model of transmission or transaxle is used. To avoid the possibility that the vehicle model may change the weight to be accorded to the various factors, it may be desirable to also sample different vehicle models in which the same model of transmission or transaxle is used.

Referring to FIG. 1, a transmission controller 10 has outputs 12 coupled to shift inputs of an automatic transmission 14. An ambient temperature sensor 16 is coupled to an input 18 of transmission controller 10, a coolant temperature sensor 20 is coupled to an input 22 of transmission controller 10, and a transmission operating temperature sensor 24 is coupled to an input 26 of transmission controller 10. A car battery 27, typically of the car in which transmission controller 10 is installed, is coupled to transmission controller 10.

Transmission controller 10 is illustratively a microcomputer and has a central processing unit 28, such as a microprocessor, and memory 30. Transmission controller 10 accumulates data of the various factors bearing on the useful life of the automatic transmission fluid and stores this data in memory 30.

FIG. 2 is a flow chart illustrating the collection and storage of transmission operating temperature data by transmission controller 10, which is illustratively stored as a histogram as shown in FIG. 13. Referring to FIG. 2, if the engine is running, the transmission operating temperature histogram routine begins at 100. The HISTSWflag is checked at 102 to determine if it is set. If not, the routine branches to END at 104 and the remaining portion of the transmission operating temperature histogram routine is not executed. Transmission controller 10 then executes the ambient temperature histogram routine beginning at 200 (FIG. 3).

If the HISTSW flag is set, the HISTRES flag is next checked at 106 to determine if a user has requested that the ambient temperature histogram data be reset. If the HISTRES flag is set, the routine branches to END at 104. If the HISTRES flag is not set, the HISTFUL flag is checked at 108 to determine if any of the transmission operating temperature histogram intervals are full. Illustratively, data for the transmission operating temperature are stored in one of twelve histogram intervals, as shown in FIG. 13. If the HISTFUL flag is set, one of the histogram intervals for the transmission operating temperature is full and the routine branches to END at 104. If the HISTFUL flag is not set, the NEWDATA flag is checked at 110 to see if there is any new data. If not, the routine branches to END at 104. If there is new data, the memory locations containing the counters for the histogram intervals for the transmission operating temperature are checked at 112 to see if any of the counters is full. If one is, the HISTFUL flag is set at 114 and the routine branches to END at 104. If none of the counters are full, transmission controller 10 reads the transmission temperature from a temporary memory location in which it was stored by the data collection routine (FIG. 10) at 116, checks to see which transmission temperature histogram interval the transmission operating temperature falls within at 118, and increments the memory location that contains the counter for that transmission operating temperature histogram interval at 120. The routine then branches to END at 104 and transmission controller 10 proceeds to execute the ambient temperature histogram routine starting at 200 (FIG. 3).

Figure 14:
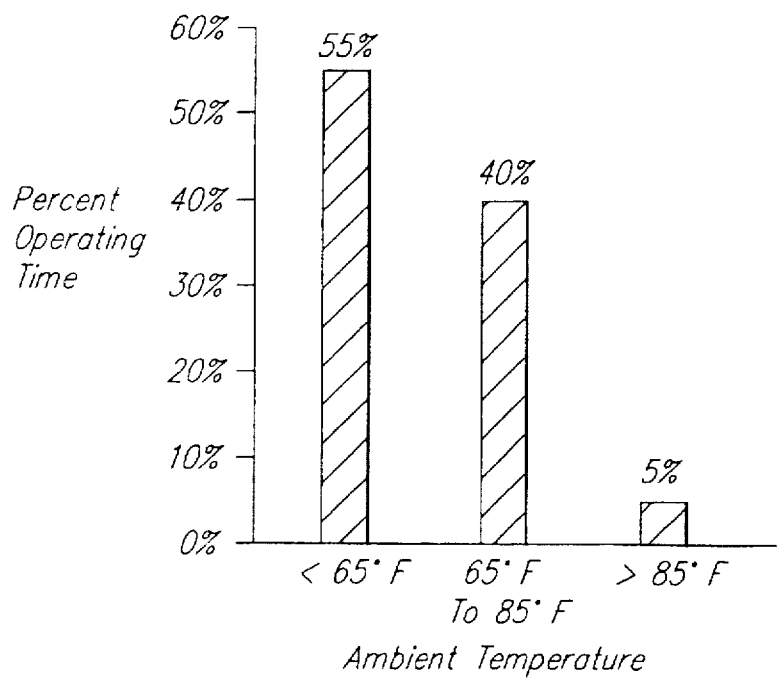
FIG. 14 is a histogram of ambient temperature.

FIG. 3 is a flow chart illustrating the collection and storage of ambient temperature data by transmission controller 10, which is illustratively stored as a histogram of the ambient temperature as shown in FIG. 14. The AMBSW flag is checked at 202 to determine if it is set. If not, the routine branches to END at 204 and the remaining portion of the ambient temperature histogram routine is not executed. Transmission controller 10 then executes the coolant temperature histogram routine beginning at 300.

If the AMBSW flag is set, the AMBRES flag is next checked at 206 to determine if a user has requested that the ambient temperature histogram data be reset. If the AMBRES flag is set, the routine branches to END at 204. If the AMBRES flag is not set, the AMBFUL flag is checked at 208 to determine if any of the ambient temperature histogram intervals are full. Illustratively, data for the ambient operating temperature are stored in one of three histogram intervals, as shown in FIG. 14. If the AMBFUL flag is set, one of the histogram intervals for the ambient temperature is full and the routine branches to END at 204. If the AMBFUL flag is not set, the NEWDATA flag is checked at 210 to see if there is any new data. If not, the routine branches to END at 204. If there is new data, the memory locations containing the counters for the histogram intervals for the ambient temperature are checked at 212 to see if any of the counters is full. If one is, the AMBFUL flag is set at 214 and the routine branches to END at 204. If none of the counters are full, transmission controller 10 reads the ambient temperature from a temporary memory location where it was stored by the data collection routine (FIG. 10) at 216, checks to see which ambient temperature histogram interval the ambient temperature falls within at 218, and increments the memory location that contains the counter for that ambient temperature histogram interval at 220. The routine then branches to END at 204 and transmission controller 10 proceeds to execute the coolant temperature histogram routine starting at 300 (FIG. 4).

Figure 4:
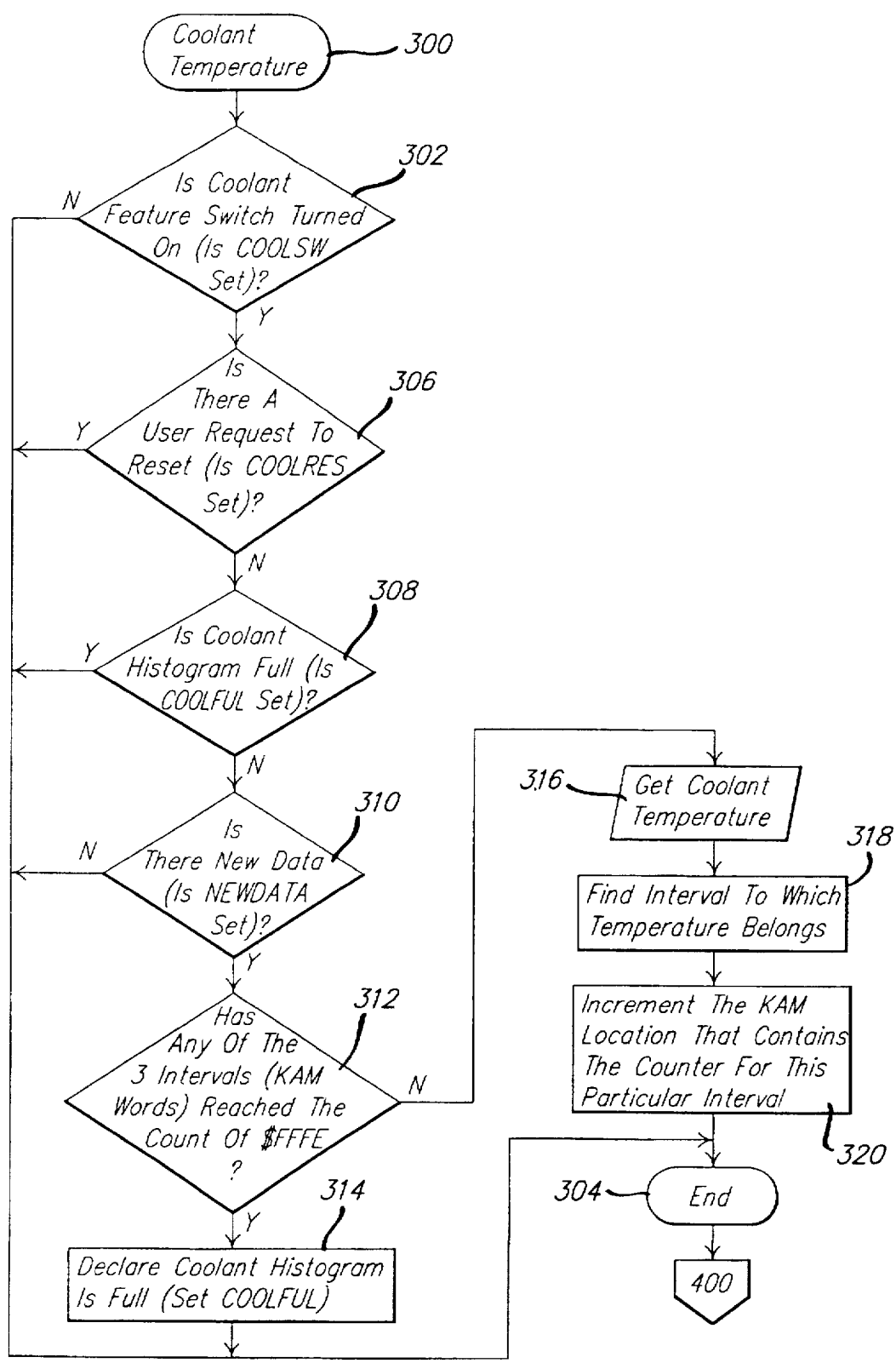
Figure 15:
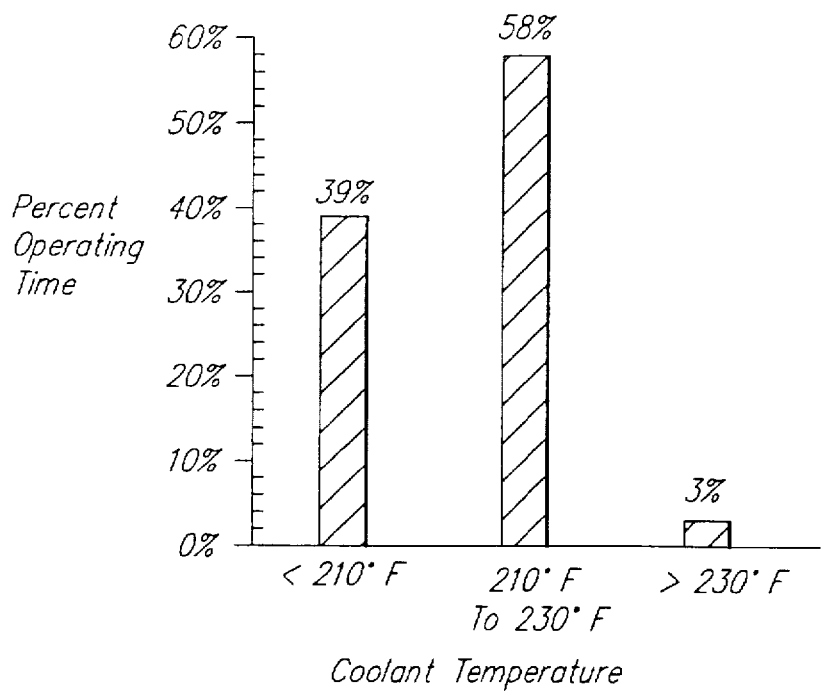
FIG. 15 is a histogram of coolant temperature.

FIG. 4 is a flow chart illustrating the collection and storage of coolant temperature data by transmission controller 10, which is illustratively stored as a histogram of the coolant temperature as shown in FIG. 15. The COOLSW flag is checked at 302 to determine if it is set. If not, the routine branches to END at 304 and the remaining portion of the coolant temperature histogram routine is not executed. Transmission controller 10 then executes the transmission temperature trend routine beginning at 400.

If the COOLSW flag is set, the COOLRES flag is next checked at 306 to determine if a user has requested that the coolant temperature histogram data be reset. If the COOLRES flag is set, the routine branches to END at 304. If the COOLRES flag is not set, the COOLFUL flag is checked at 308 to determine if any of the coolant temperature histogram intervals are full. Illustratively, data for the coolant temperature are stored in one of three histogram intervals, as shown in FIG. 15. If the COOLFUL flag is set, one of the histogram intervals for the coolant temperature is full and the routine branches to END at 304. If the COOLFUL flag is not set, the NEWDATA flag is checked at 310 to see if there is any new data. If not, the routine branches to END at 304. If there is new data, the memory locations containing the counters for the histogram intervals for the coolant temperature are checked at 312 to see if any of the counters is full. If one is, the COOLFUL flag is set at 314 and the routine branches to END at 304. If none of the counters are full, transmission controller 10 reads the coolant temperature from a temporary memory location where it was stored by the data collection routine (FIG. 10) at 316, checks to see which coolant temperature histogram interval the coolant temperature falls within at 318, and increments the memory location that contains the counter for that coolant temperature histogram interval at 320. The routine then branches to END at 204 and transmission controller 10 proceeds to execute the transmission temperature trend routine starting at 400 (FIG. 5).

Figure 5:
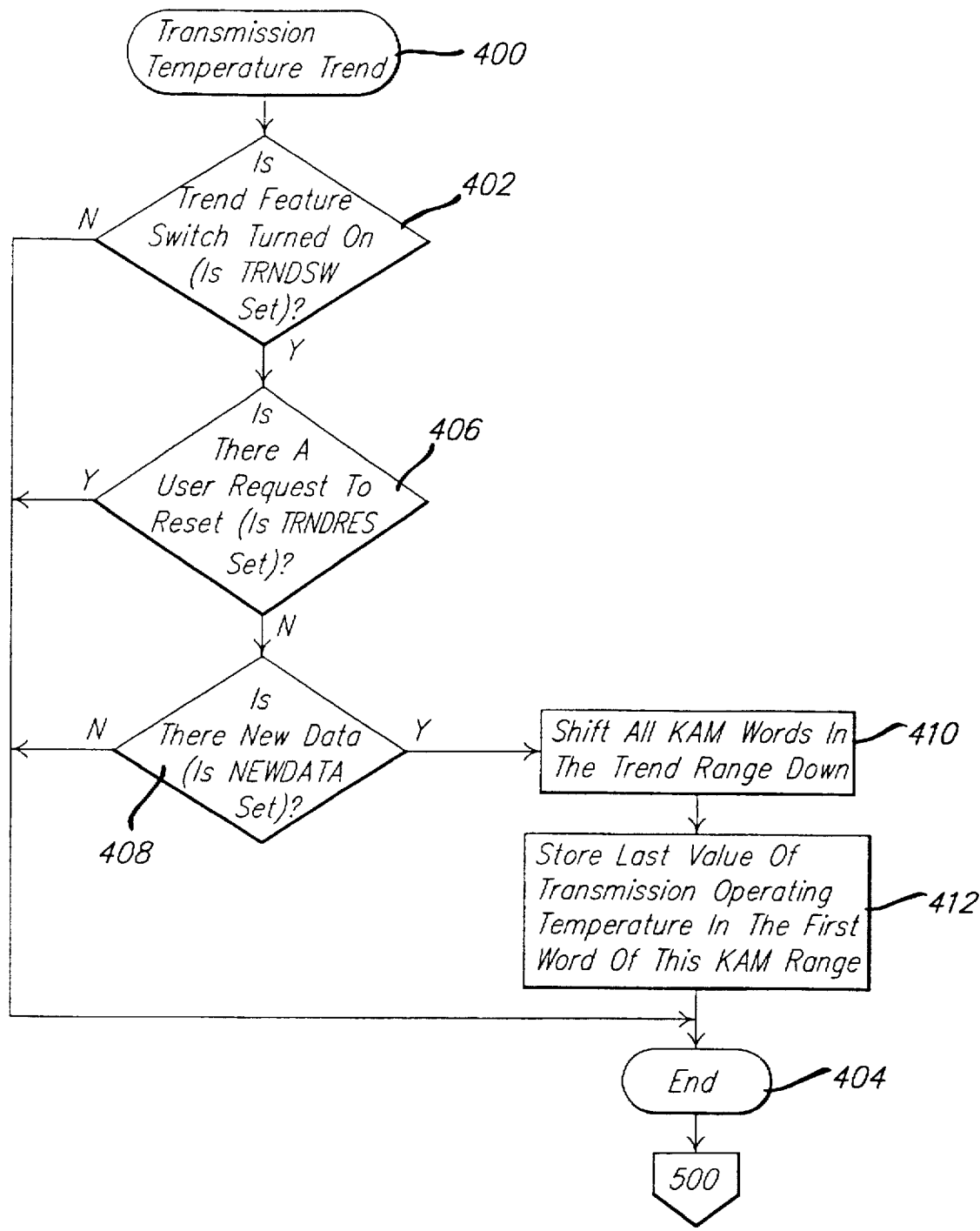
Figure 5:
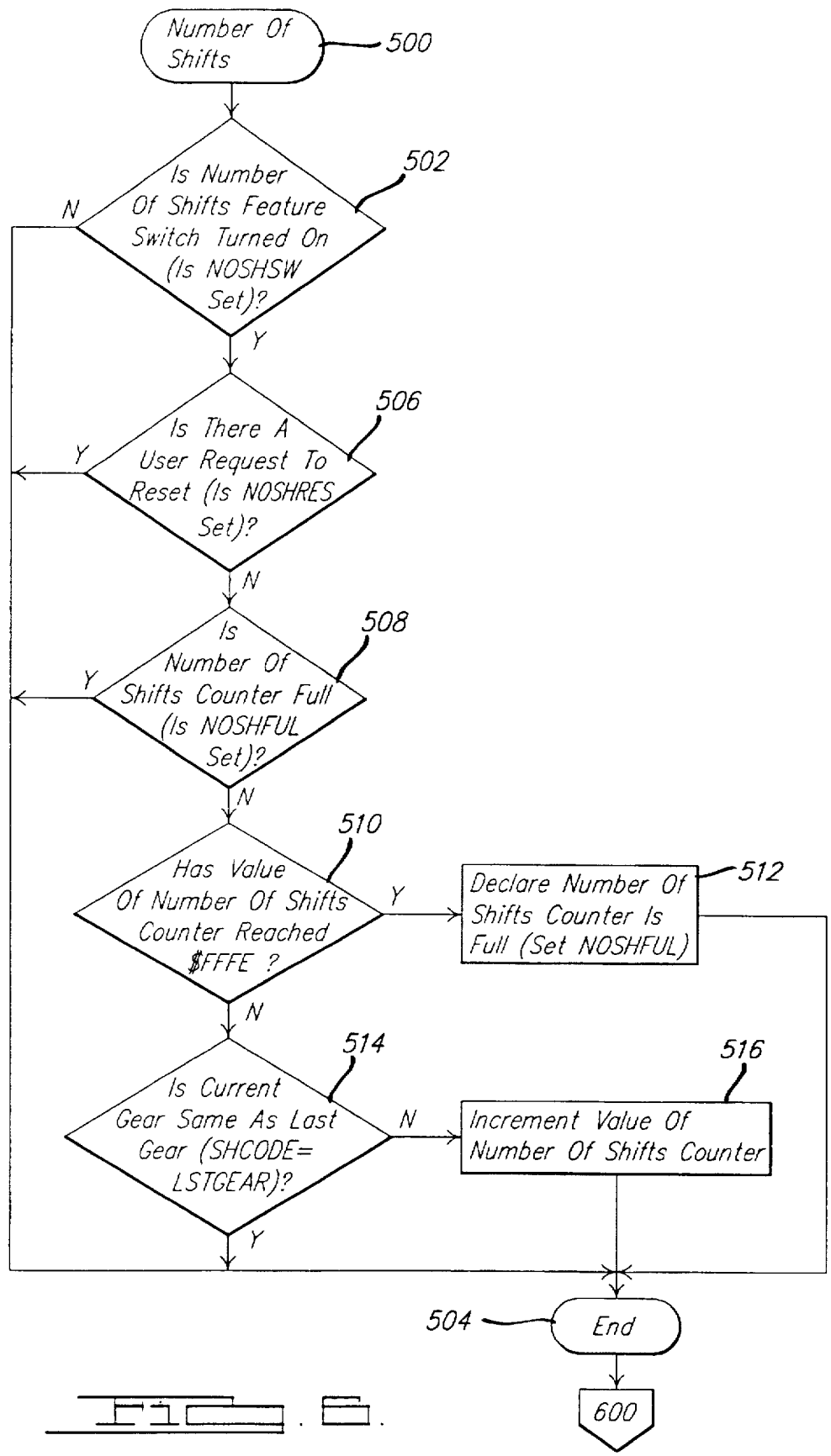

FIG. 5 is a flow chart illustrating the collection and storage of transmission operating temperature trend data by transmission controller 10. The trend data is the last one and one-half hours of transmission operating temperatures. Illustratively, when transmission operating temperature trend data is being collected, transmission controller 10 stores the last forty readings of the transmission operating temperature in memory 30 in a LIFO (last in, first out) table. The TRNDSW flag is checked at 402 to determine if it is set. If not, the routine branches to END at 404 and the remaining portion of the transmission operating temperature trend data routine is not executed. Transmission controller 10 then executes the number of shifts routine beginning at 500.

If the TRNDSW flag is set, the TRNDRES flag is next checked at 406 to determine if a user has requested that the transmission temperature trend data be reset. If the TRNDRES flag is set, the NEWDATA flag is checked at 408 to see if there is any new data. If not, the routine branches to END at 404. If there is new data, all the memory locations in the FIFO table in which the transmission operating temperature trend data are stored are shifted down at 410 and the last transmission operating temperature input by transmission controller 10 from transmission temperature sensor 14 is stored at 412 in the first or entry memory location of the LIFO table. The transmission controller 10 then proceeds to execute the number of shifts routine beginning at 500.

FIG. 6 is a flowchart illustrating the collection and storage of number of shifts by transmission controller 10. The NOSHSW flag is checked at 502 to determine if it is set. If not, the routine branches to END at 504 and the remaining portion of the number of shifts routine is not executed. Transmission controller 10 then executes the time in EMCC routine beginning at 600.

If the NOSHW flag is set, the NOSHRES flag is next checked at 506 to determine if a user has requested that the number of shifts counter be reset. If the NOSHRES flag is set, the routine branches to END at 504. If the NOSHRES flag is not set, the NOSHFUL set flag is checked at 508 to determine if the number of shifts counter is full. If the NOSHFUL flag is set, the number of shifts counter is full and the routine branches to END at 504. If the NOSHFUL is not set, the value of the number of shifts counter is checked at 510 to see if it has reached its maximum value. If it has, the NOSHFUL flag is set at 512 and the routine then goes to END at 504. If the number of shifts counter has not reached its maximum value, the routine next checks to see if the current gear is the same as the last gear at 514. As is known, since transmission controller 10 controls the shifting of transmission 12, transmission controller 10 has data stored in its memory 30 which indicates the last gear the transmission 12 was in (LSTGEAR) and the current gear (SHCODE). If the current gear is the same as the last gear, transmission 12 has not shifted and the routine proceeds to END at 504. If the current gear is not equal to the last gear, then transmission 12 has shifted and the number of shifts counter is incremented at 516. The routine then branches to END at 504. Transmission controller 10 then proceeds to execute the time in EMCC routine beginning at 600.

Figure 7:
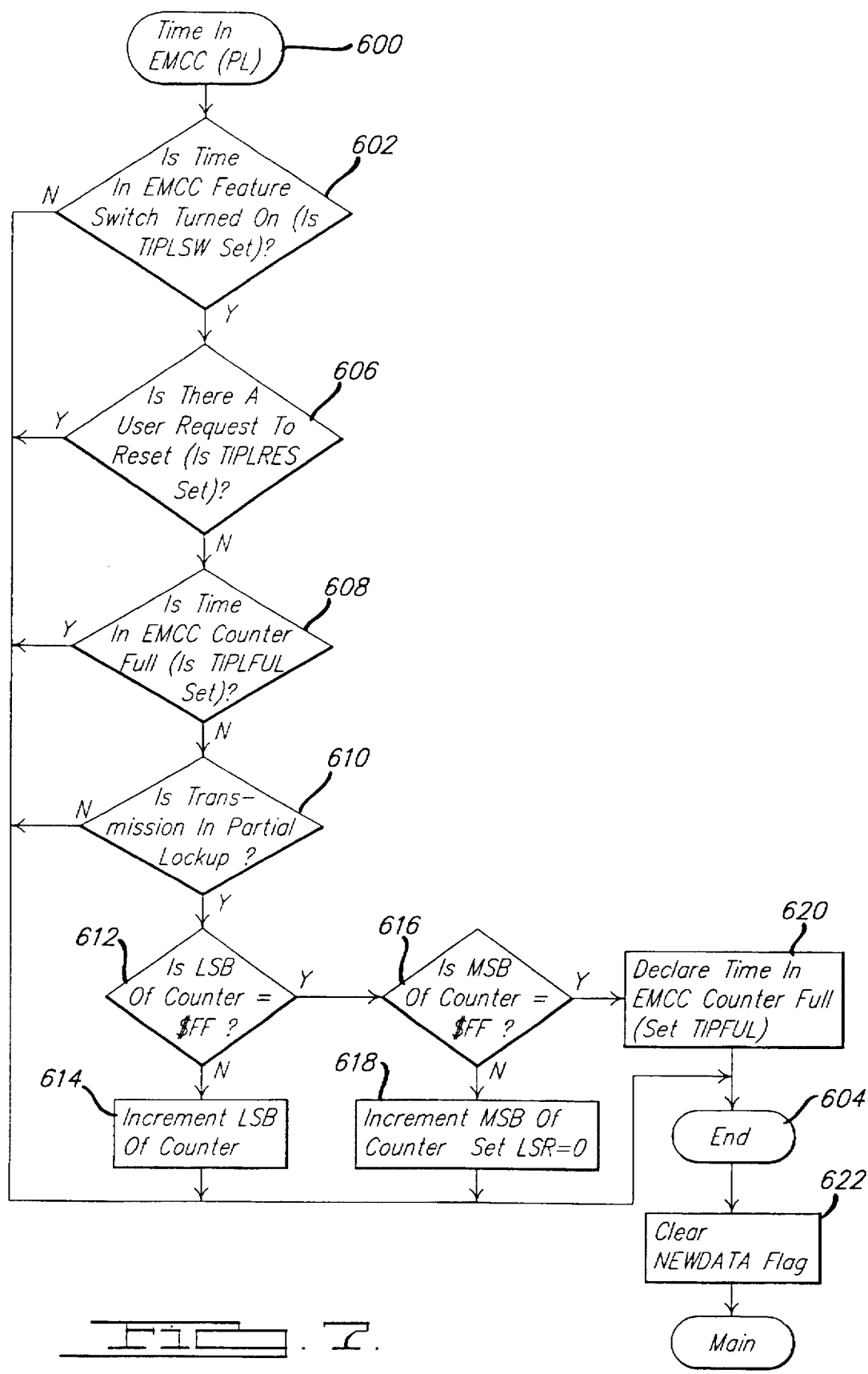

FIG. 7 is a flow chart illustrating the collection and storage of time in EMCC by transmission controller 10. Illustratively, transmission controller 10 loops through this routine every 28 msec so time is determined by counting the number of times transmission controller 10 has looped through this routine and multiplying by 28 msec. Referring to FIG. 7, the TIPLSW flag is checked at 602 to determine if it is set. If not, the routine branches to END at 604 and the remaining portion of the time in EMCC routine is not executed and the routine branches to the step of clearing the NEWDATA flag at 622 and transmission controller 10 then branches back to the main routine for transmission controller 10.

If the TIPSW flag is set, the TIPLES flag is next checked at 606 to determine if a user has requested that the time in EMCC data be reset. If the TIPLES flag is set, the routine branches to END at 604. If the TIPLES flag is not set, the TIPLFUL flag is checked at 608 to determine if the time in EMCC counter is full. If the TIPLFUL flag is not set, the routine 10 checks to see if transmission 14 is in EMCC (partial lock-up) at 610. If transmission 14 is not in EMCC, the routine branches to END at 604. If the transmission is in EMCC, the routine next checks to see if the least significant byte (LSB) of the EMCC counter is full at 612. If the LSB is not full, the routine increments the LSB at 614 and continues to END at 604. If the LSB is full, the routine checks the most significant byte (MSB) of the EMCC counter to see if it is full at 616. If the MSB is full, the routine declares that the time in EMCC is full at 620 by setting the TIPFUL flag. The routine then continues to END at 604. If the MSB is not full, the routine then increments the MSB and sets the LSB to zero at 618. The routine then continues to END at 604 and, after clearing the NEWDATA flag at 622, branches back to the main routine of transmission controller 10.

FIGS. 8–12 are flow charts showing a backup to static memory (EE), such as an electronically erasable memory, routine (FIG. 8), a user reset request routine (FIG. 9), a data collection routine (FIG. 10), a powerup initialization routine (FIG. 11), and a battery disconnect initialization routine (FIG. 12). Illustratively, memory 30 can include a static memory and a dynamic memory.

Referring to FIG. 8, the backup to EE routine first checks to see if the logged data is to be backed up to EE by checking if the BKUPSW switch is set at 702. If it is not, the routine branches to end at 704. If the BKUPSW switch is set, the ENGR1 5M flag is checked at 706 to determine whether the engine has been running for at least fifteen minutes. If the ENGR1 5M flag is not set, the engine has not been running for at least fifteen minutes and the routine branches to end at 704. If the ENGR15M flag is set, the routine next checks at 708 to see if transmission controller 10 is in the second phase of powerdown. The first phase of powerdown occurs when transmission controller 10 detects a fault and sets a diagnostic code. The second phase of powerdown occurs when power to transmission controller 10 is disconnected, such as by the opening of a relay. If not, the routine branches to end at 704. If transmission controller 10 is in the second phase of powerdown, the routine then backs up to EE by writing the KAM locations in which the Transmission Temperature Histogram, the Ambient Temperature Histogram, the Coolant Temperature Histogram, the Number of Shifts and the Time in EMCC data are stored to EE at 710. The routine then branches back to the main routine of transmission controller 10.

Figure 9:
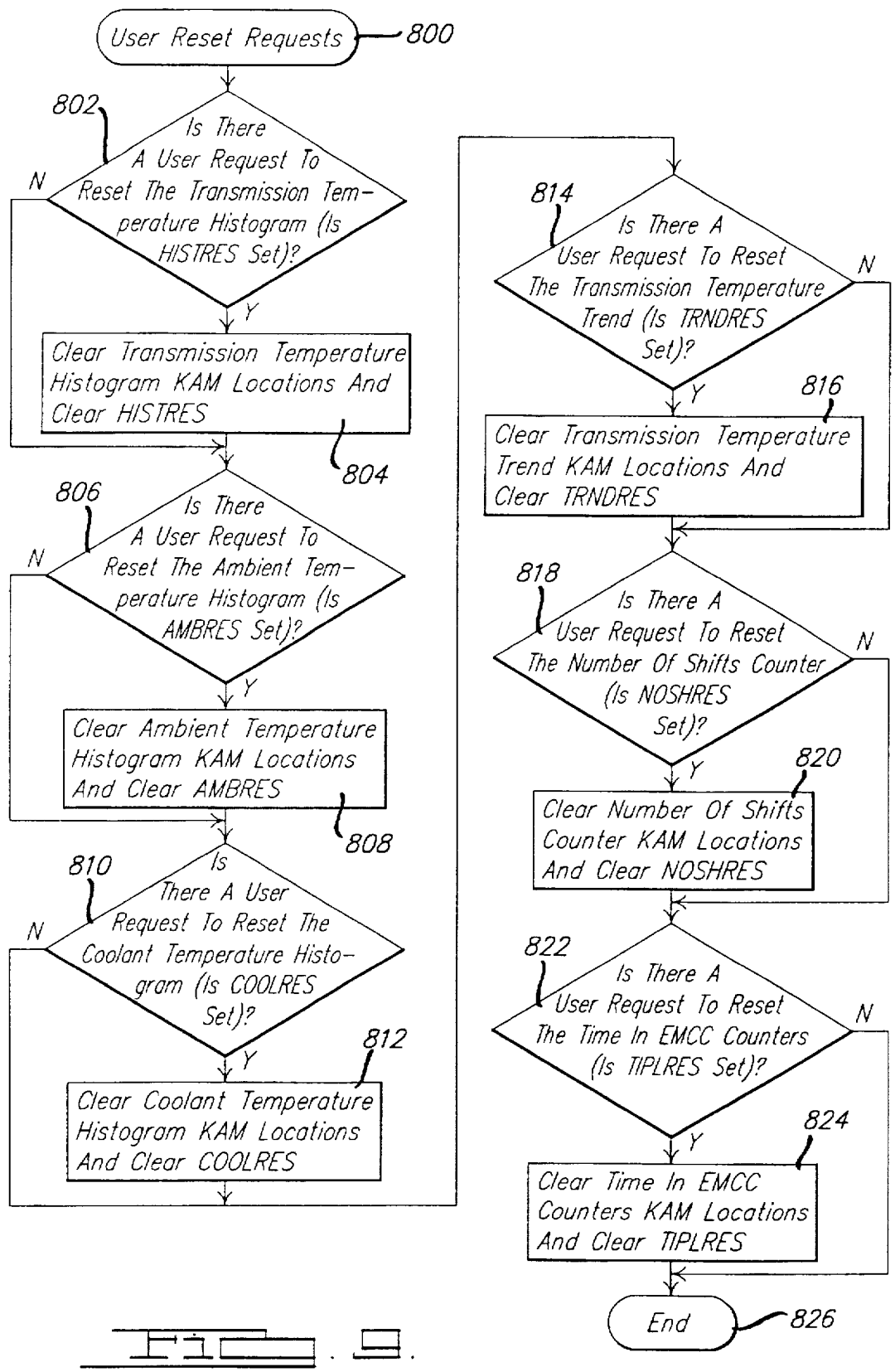

With reference to FIG. 9, the user reset request routine first checks to see if there has been a user request to reset the transmission temperature histogram by checking to see if the HISTRES flag is set at 802. If the HISTRES flag is not set, the routine branches to 806. If the HISTRES flag is set, the routine clears the KAM locations in which the transmission temperature histogram is stored and the HISTRES flag at 804 and then continues to 806.

At 806, the routine checks if there has been a user request to reset the ambient temperature histogram by checking to see if the AMBRES flag is set. If the AMBRES flag is set, the routine clears the KAM locations in which the ambient temperature histogram is stored and the AMBRES flag at 808 and continues to 810. If the AMBRES flag is not set, the routine branches to 810.

At 810, the routine checks to determine whether there has been a user request to reset the coolant temperature histogram by checking to see if the CHECKRES flag has been set. If the CHECKRES flag has been set, the routine clears the KAM locations in which the coolant temperature histogram is stored and the CHECKRES flag at 812 and continues to 814. If the CHECKRES flag is not set, the routine branches to 814.

AT 814, the routine checks to determine if there has been a user request to reset the transmission temperature trend by checking to see if the TRNDRES flag is set. If the TRNDRES flag is set, the routine clears the KAM locations in which the temperature trend data has been stored and the TRNDRES flag at 816 and continues to 818. If the TRNDRES flag is not set, the routine branches to 818.

At 818, the routine checks to determine if there has been a user request to reset the number of shifts counter by checking to see if the NOSHRES flag is set. If the NOSHRES flag is set, the routine clears the KAM locations in which the number of shifts data has been stored and the NOSHRES flag at 820 and continues to 822. If the NOSHRES flag is not set, the routine branches to 822.

At 822, the routine checks to see if there has been a user request to reset the time in EMCC counters by checking to see if the TIPLRES flag is set. If the TIPLRES flag is set, the routine clears at 824 the KAM locations in which the time in EMCC data has been stored and the TIPLRES flag and continues to END at 826. If the TIPLRES flag is not set, the routine branches to END at 826. Transmission controller 10 then branches back to the main routine of transmission controller 10.

Referring to FIG. 10, the data collection routine reads the ambient transmission temperature from temperature sensor 22, the ambient temperature from temperature sensor 16 and the coolant temperature from temperature sensor 20 at 902 and then stores this data in temporary memory locations in memory 30 of transmission controller 10 at 904. The routine then sets the NEWDATA flag at 906 indicating that transmission controller 10 has acquired new data and continues to END at 908. Transmission controller 10 then branches back to the main routine of transmission controller 10.

Figure 11:
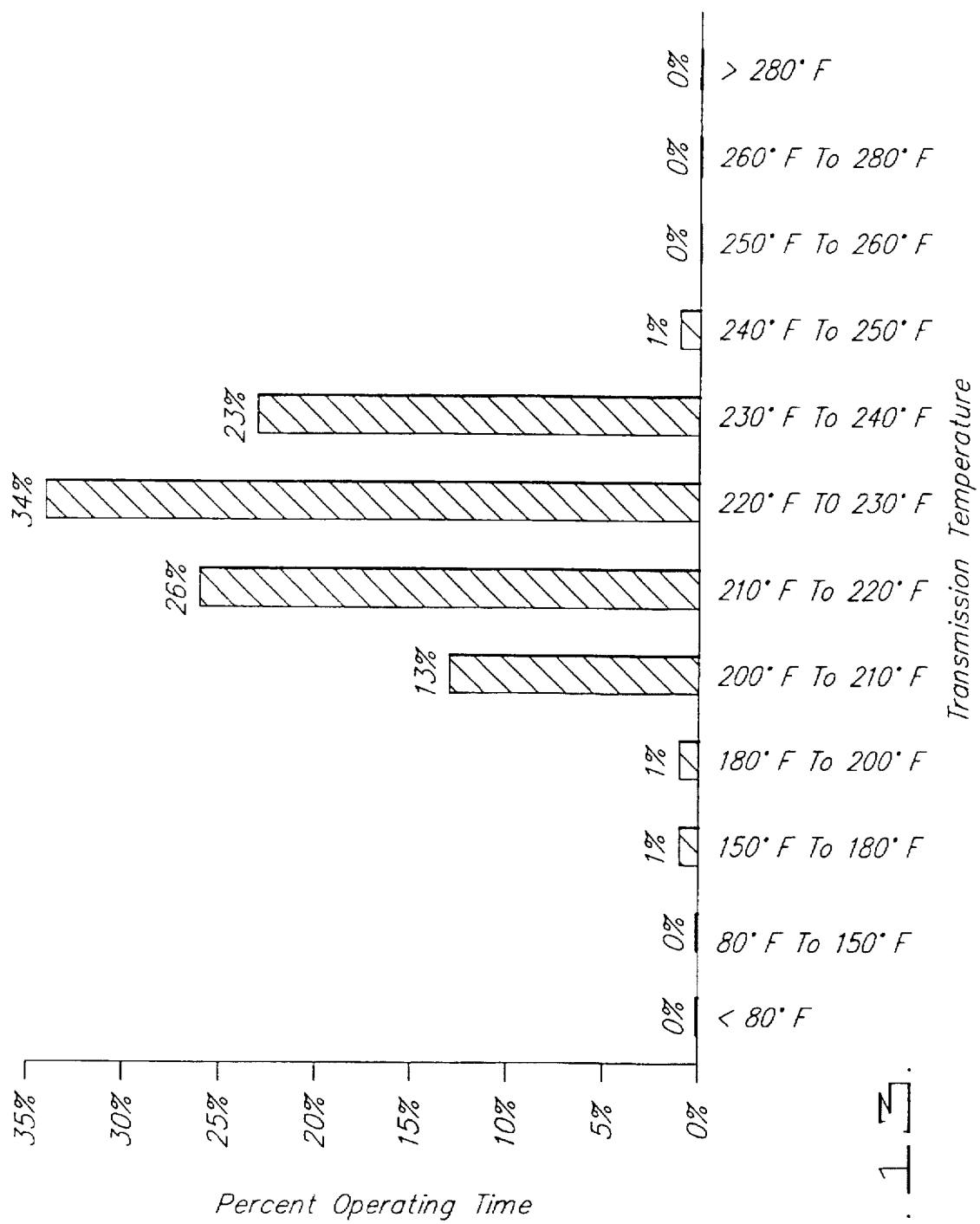

Referring to FIG. 11, upon powerup, transmission controller 10 branches to the powerup initialization routine starting at 1000. The powerup initialization routine stores at 1002 the "neutral" shift code in the memory location in memory 30 that contains the last gear data. The routine then continues to END at 1004. Transmission controller 10 then branches back to the main routine of transmission controller 10.

Referring to FIG. 12, a battery disconnect initialization routine that transmission controller 10 executes each time it determines that the car battery has been disconnected from transmission controller 10 is shown. Transmission controller 10 first determines whether the car battery 27 (FIG. 1) has been disconnected from transmission controller 10 at 1102. If the car battery 27 has not been disconnected from transmission controller 10, transmission controller 10 branches to END at 1104. If the car battery 27 has been disconnected from transmission controller 10, transmission controller 10 next determines whether it is a new or replacement controller for that car at 1106. If not, transmission controller 10 restores the counters for the histograms from a back-up memory, such as an electronically erasable memory at 1108 and then branches to END at 1104. If transmission controller 10 is a new or replacement controller for the car in which it is installed, then transmission controller 10 clears all the counters for the histograms at 1110 and then branches to END at 1104.

To accumulate adequate historical data on the factors bearing on automatic transmission life, the operation of a multiplicity of each type of automatic transmission or automatic transmission is monitored and data collected by the automatic transmission controller 10 coupled to each automatic transmission or automatic transaxle. A sample of automatic transmission fluid from each automatic transmission or automatic transaxle is periodically analyzed to determine its characteristics. When the automatic transmission fluid in an automatic transmission or automatic transaxle reaches the end of its useful life, the data is dumped, the automatic transmission fluid changed, the histograms reset and the process repeated. Alternatively, the automatic transmission fluid is changed at periodic intervals, such as thirty thousand miles, at which time the old automatic transmission fluid is analyzed, the data dumped, and the histograms reset. In this regard, when the data is dumped, a reading of the accumulated mileage during which the automatic transmission fluid was in use is also taken, such as by reading the mileage from the engine controller and subtracting from it the mileage on the vehicle when the automatic transmission fluid was put into the automatic transmission or the automatic transaxle.

After data has been accumulated for a number of vehicles having a specific type of automatic transmission or automatic transaxle, this data is evaluated and weighted constants for each of the factors bearing on automatic transmission life determined. Once the weighted constants are determined, the automatic transmission controllers 10 for that type of automatic transmission or automatic transaxle are programmed to accumulate the data for the factors bearing on automatic transmission fluid, as discussed above, and to determine the remaining useful life of the automatic transmission fluid based on the accumulated data for the factors bearing on automatic transmission life and the weighted constants for the factors. For example, automatic transmission controller 10 can be programmed to determined a remaining life index (RLI) of the automatic transmission fluid, such as:

RLI=MLI−[a×transmission operating temperature+b× ambient temperature+c×coolant temperature+d×number of shifts+e×time in EMCC+f×shear during EMCC+g×shear during shifts+h×accumulated mileage] where a–h are the weighed constants and MLI is a maximum life index, a constant for each fluid type/vehicle combination, determined from steady-state driving at normal operating temperatures. When the automatic transmission controller 10 determines that the automatic transmission fluid has reached the end of its useful life, it alerts the operator of the vehicle that the automatic transmission fluid needs to be changed, such as by activating an indicator 32 coupled to automatic transmission controller 10 (FIG. 1).

Although the invention has been described in detail with reference to certain preferred embodiments and specific examples, variations and modification exist within the scope and spirt of the invention as described and as defined in the following claims.

What is claimed is:

1. A method of determining the remaining useful life of automatic transmission fluid used in an automatic transmission or automatic transaxle controlled by a programmable electronic controller, comprising the steps of:

a. monitoring in-vehicle operation of a multiplicity of the same type of automatic transmissions or automatic transaxles as the first recited automatic transmission or automatic transaxle and collecting data on factors that bear on the useful life of automatic transmission fluid wherein one factor is time during electronic modulation of converter clutch (EMCC);

b. deriving weighted constants for each factor based on the accumulated data;

c. programming the programmable electronic controller to monitor the operation of the first recited automatic transmission or automatic transaxle and collect data on the factors that bear on the useful life of automatic transmission fluid including time during EMCC; and d. programming the programmable electronic controller to determine the remaining useful life of the automatic transmission fluid in the first recited automatic transmission or transaxle based on the collected data and weighted constants, including the collected data and weighted constant for time during EMCC factor.

2. The method of claim 1 and further including the step of programming the electronic controller to activate an indicator coupled to the programmable controller when the useful life of the automatic transmission fluid has been reached to alert an operator of the vehicle to change the automatic transmission fluid.

3. The method of claim 1 wherein the factors bearing of the useful life of the automatic transmission fluid include, in addition to time during EMCC, accumulated mileage, the temperature of the automatic transmission or automatic transaxle, the ambient temperature, coolant temperature, number of shifts, shear during EMCC, and shear during shifts, and the step of programming the programmable electronic controller to determine the remaining useful life of the automatic transmission fluid comprises programming it to do so based on at least one of these factors and its weighted constant in addition to the factor of time during EMCC and its weighted constant.

4. The method of claim 1 wherein the factors bearing on the useful life of the automatic transmission fluid include, in addition to time during EMCC, accumulated mileage, the operating temperature of the automatic transmission or automatic transaxle, the ambient temperature, coolant temperature, number of shifts, shear during EMCC, and shear during shifts, and the step of programming the programmable electronic controller to determine the remaining useful life of the automatic transmission fluid comprises programming it to do so based on these factors and their weighted constants in addition to the factor of time during EMCC and its weighted constant.

5. The method of claim 1 wherein the factors bearing on the useful life of the automatic transmission fluid include, in addition to time during EMCC, the operating temperature of the automatic transmission or automatic transaxle, shear during EMCC, and shear during shifts, and the step of programming the programmable electronic controller to determine the remaining useful life of the automatic transmission fluid comprises programming it to do so based on these factors and their weighted constants in addition to the factor of time during EMCC and its weighted constant.

* * * * *